(12) United States Patent
Clarke

(10) Patent No.: US 10,709,835 B2
(45) Date of Patent: Jul. 14, 2020

(54) SYRINGE PUMP AND ARRAY OF SYRINGE PUMPS WITH MULTI-ZONE ELECTRONIC DISPLAY

(76) Inventor: Christopher Clarke, Surrey (GB)

( * ) Notice: Subject to any disclaimer, the term of this patent is extended or adjusted under 35 U.S.C. 154(b) by 1395 days.

(21) Appl. No.: 13/988,471

(22) PCT Filed: Nov. 19, 2010

(86) PCT No.: PCT/EP2010/067852
§ 371 (c)(1),
(2), (4) Date: Aug. 29, 2013

(87) PCT Pub. No.: WO2012/065649
PCT Pub. Date: May 24, 2012

(65) Prior Publication Data
US 2014/0046296 A1      Feb. 13, 2014

(51) Int. Cl.
| | | |
|---|---|---|
| *A61M 5/14* | (2006.01) | |
| *A61M 5/145* | (2006.01) | |
| *G06F 19/00* | (2018.01) | |
| *A61M 5/31* | (2006.01) | |

(52) U.S. Cl.
CPC ....... *A61M 5/1456* (2013.01); *G06F 19/3468* (2013.01); *A61M 5/1408* (2013.01); *A61M 5/1409* (2013.01); *A61M 5/1415* (2013.01); *A61M 2005/3125* (2013.01); *A61M 2005/3126* (2013.01); *A61M 2205/502* (2013.01); *A61M 2205/505* (2013.01); *A61M 2205/587* (2013.01); *A61M 2209/084* (2013.01); *A61M 2209/086* (2013.01)

(58) Field of Classification Search
CPC .................. A61M 5/1456; A61M 5/14; A61M 2205/505; A61M 2205/502; A61M 2005/3125; A61M 2005/3126; G06F 19/3468
See application file for complete search history.

(56) References Cited

U.S. PATENT DOCUMENTS

| | | | | |
|---|---|---|---|---|
| 4,424,720 A | * | 1/1984 | Bucchianeri | A61M 5/1456 128/DIG. 1 |
| 4,838,857 A | * | 6/1989 | Strowe | A61M 5/1456 128/DIG. 12 |
| 5,139,484 A | * | 8/1992 | Hazon | A61M 5/1456 128/DIG. 1 |
| 5,814,015 A | * | 9/1998 | Gargano | A61M 5/1456 604/67 |
| 2003/0001488 A1 | * | 1/2003 | Sundahl | H01L 51/529 313/483 |

(Continued)

*Primary Examiner* — Rebecca E Eisenberg
*Assistant Examiner* — Weng Lee
(74) *Attorney, Agent, or Firm* — Morgan, Lewis & Bockius LLP

(57) ABSTRACT

An infusion pump for infusing a fluid from a syringe, the syringe comprising a syringe barrel and a syringe plunger comprising a piston, a plunger stem and a plunger flange, wherein the infusion pump comprises a housing having a display, a syringe retainer for retaining the syringe in place and a plunger driver for pushing the syringe plunger to expel fluid from the syringe, characterized in that the syringe retainer retains the syringe in a position such that at least a visible part of the display is located behind the syringe barrel. An array of infusion pumps and a docking station for docking infusion pumps is also described.

20 Claims, 4 Drawing Sheets

(56) References Cited

U.S. PATENT DOCUMENTS

2005/0148867 A1* 7/2005 Neer ................. A61M 5/14546
 600/431
2006/0184122 A1* 8/2006 Nemoto ................ A61M 5/007
 604/154

* cited by examiner

SYRINGE PUMP AND ARRAY OF SYRINGE PUMPS WITH MULTI-ZONE ELECTRONIC DISPLAY

CROSS-REFERENCE TO RELATED APPLICATIONS

This application is a national stage entry under 35 U.S.C. §371(c) claiming priority benefit from International Patent Application No. PCT/EP2010/067852 filed Nov. 19, 2010.

FIELD OF THE INVENTION

The present invention relates to an infusion pump and in particular to a syringe pump having an improved user display.

BACKGROUND OF THE INVENTION

An infusion pump is a medical device commonly used to infuse fluids or medicaments to a patient.

In particular, an infusion syringe pump is a device which drives a syringe plunger of a syringe at a predetermined rate, thereby expelling fluid from the syringe and then on through a tube to the patient. Typically, syringe pumps comprise a motor that drives a screw or gear mechanism to move a pushing surface (drive head) at a controllable rate. The rate of movement of the pushing surface or drive head can be predetermined by a medical practitioner such as a nurse in order to infuse fluid from the syringe at the desired rate of administration. The rate of flow can be precisely controlled and extremely low rates of infusion can be achieved, for example 0.1 ml per hour infusions, which could not be achieved using gravity infusion (i.e. a so-called "drip").

A syringe pump typically comprises a body or housing which is adapted to receive the non-moving body of a syringe, i.e. the syringe barrel. This portion of the housing is known as the syringe cradle. There may be a groove in the syringe cradle in which a flange of the syringe barrel can be located in order to immobilise the syringe barrel from longitudinal movement during longitudinal movement of the syringe plunger within the barrel.

The syringe plunger has a plunger flange which is connected to the syringe piston by a syringe plunger stem. When mounting a syringe in the syringe pump, the plunger flange is held beside the syringe plunger drive head which may additionally be provided with a retaining arm or arms for holding the syringe plunger at a correct centred position. A syringe barrel clamp or clip may also be provided to clamp the barrel in a predetermined position.

As known in the art, the drive head is connected to a screw drive mechanism for connecting the linear motion of the screw drive mechanism to the syringe plunger in order to empty the syringe.

The prior art syringe pump is typically provided with a control panel or buttons for the user to program the desired infusion. The user can typically input the drug to be infused, the syringe brand and size and the desired infusion rate or duration of infusion. The device is also provided with a display which firstly allows an operator to view his or her inputs from the control panel as he or she programs the pump, and also provides information to the operator whilst infusion is in progress. Such information could include, for example, "infusion time remaining" (i.e. time remaining until all fluid is expelled from the syringe) or "infusion volume remaining" (i.e. VTBI="volume to be infused").

Typically, manufacturers have attempted to keep syringe pumps as small as possible for ease of mounting on a mounting frame, easy handling and in order to save space around a patient's bedside. One way to achieve this in the past has been to provide displays which have a large width but low height i.e. relatively long but thin displays. Whilst these custom displays can be considerably more costly than displays of standard size which are commercially available from suppliers "off the shelf", the displays of standard size may be of unsuitable proportion for a compact syringe pump.

In addition, a practitioner typically wants to see both the electronic display but also the syringe barrel itself to provide an immediate visual representation as to the state of the infusion.

It is therefore an object of the present invention to provide a syringe pump having a display of cost-effective size whilst also providing space for the syringe barrel itself to be viewed.

SUMMARY OF INVENTION

According to the present invention, there is provided an infusion pump for infusing a fluid from a syringe, the syringe comprising a syringe barrel and a syringe plunger comprising a piston, a plunger stem and a plunger flange, wherein the infusion pump comprises a housing having a display, a syringe retainer for retaining the syringe in place and a plunger driver for pushing the syringe plunger to expel fluid from the syringe, characterised in that the syringe retainer retains the syringe in a position such that at least a visible part of the display is located behind the syringe barrel.

Preferably, the display comprises an LCD panel.

Advantageously, the display has a diagonal length of about 5.7 inches (144-145 mm).

Conveniently, the display is backlit.

Preferably, the display is additionally a touchscreen.

Advantageously the display is separated into at least two zones, preferably wherein each display zone is a different colour or brightness.

Conveniently at least part of one zone is located on the part of the display located behind the syringe barrel.

Preferably, the size and layout of the at least two zones are dimensioned and positioned in response to the dimensions of the syringe, such that the at least one part of one zone is generated on the part of the display located behind the syringe barrel.

Advantageously the display extends substantially from the top of a front face of the housing to the bottom of a front face of the housing.

Conveniently the display is capable of displaying infusion data selected from the list including drug name, syringe volume or size, syringe manufacturer, time, date, desired infusion rate, actual infusion rate, system pressure, fluid volume already infused, fluid volume still to be infused, infusion time already elapsed and/or infusion time remaining.

Preferably the infusion data is selected from fluid volume already infused and/or infusion time already elapsed and wherein said data is displayed on the screen in an area proximal a part of the syringe barrel containing no fluid.

More preferably the infusion data is selected from fluid volume still to be infused and/or infusion time remaining and wherein said data is displayed on the screen in an area proximal a part of the syringe barrel containing fluid.

The invention also provides an array of infusion pumps according to the invention, wherein the displays of each pump in the array are aligned in a vertical direction.

Preferably each pump in the array is in close proximity to the next adjacent pump.

The invention also provides a docking station configured to dock with at least one infusion pump according to the invention, wherein the docking station and the pump each have cooperating locating means to locate the pump in place, and wherein the docking station optionally includes a computer controller.

BRIEF DESCRIPTION OF DRAWINGS

Embodiments of the present invention are described below with reference to the accompanying drawings in which.

DETAILED DESCRIPTION OF PREFERRED EMBODIMENT

Figure 1:
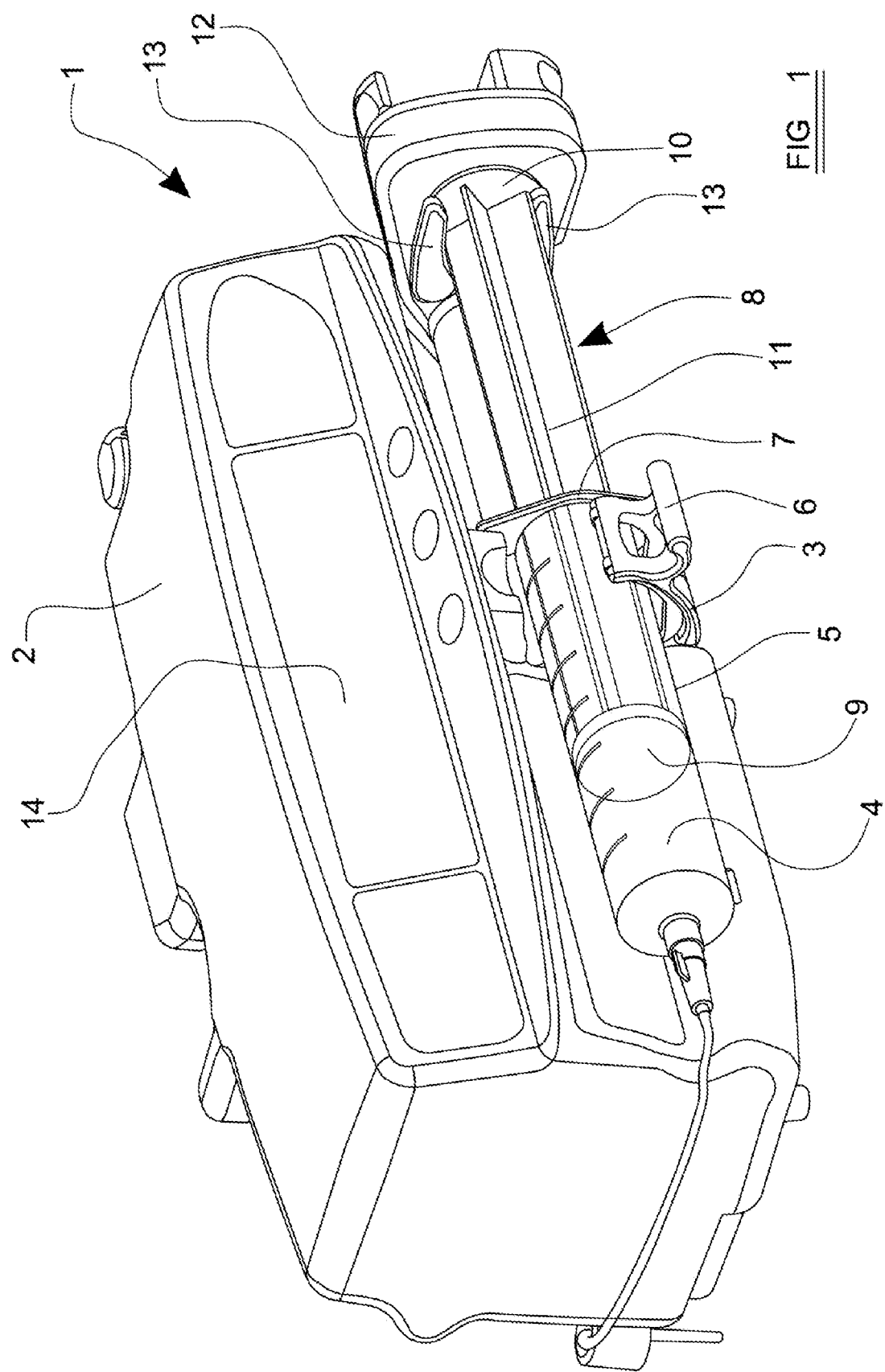
FIG. 1 is a perspective view of a prior art syringe pump.

FIG. 1 shows the typical components of a syringe pump 1 as known in the art. There is provided a housing 2 having a syringe cradle 3 therein which is of appropriate size for receiving a syringe 4, in particular the syringe barrel 5 thereof. In the example shown, there is a clip 6 provided to support the syringe barrel 5 in the syringe cradle 3 and a groove which receives the flange 7 of the syringe barrel 5. The prior art syringe pump 1 as shown is in a state either before or during infusion where the syringe plunger 8 is extended out of the syringe barrel 5. The syringe plunger 8 terminates with a syringe piston 9 at one end, which forces fluid from the syringe 4 and a syringe flange 10 at an opposing end, connected by the syringe plunger stem 11. The syringe flange 10 is pushed via the driver head 12 when in use, which forces the syringe piston 9 through the syringe barrel 5 thereby forcing liquid through the end of the syringe 4. The syringe flange 10 may additionally be supported or clamped by one or more retaining arms 13.

As well as operating buttons or switches, which the operator uses to activate and program the syringe pump 1, there is a display screen 14. In prior art devices, the display screen 14 may be a simple LCD (liquid crystal display) having a small number of segments, for example seven segments in a figure-of-eight configuration per character, adapted to display a small number of alphanumeric characters. The display may be monochromatic, for example, it might only display red, green or grey/black characters.

Alternatively, the display 14 might be a more complicated liquid crystal display capable of displaying more characters or more complicated characters. The LCD may be backlit, for example, using light emitting diodes (LEDs).

As stated above, LCDs as known in the art and incorporated into prior art syringe pumps 1 have been customised into relatively long (greater width than height) configurations as shown in FIG. 1 in order to display sufficient information whilst saving space on the front housing 2 of the pump 1. Such customised displays can be more expensive for a manufacturer to produce than display modules that are already commercially available and can simply be incorporated into the syringe pump 1 at the manufacturing stage.

Figure 2:
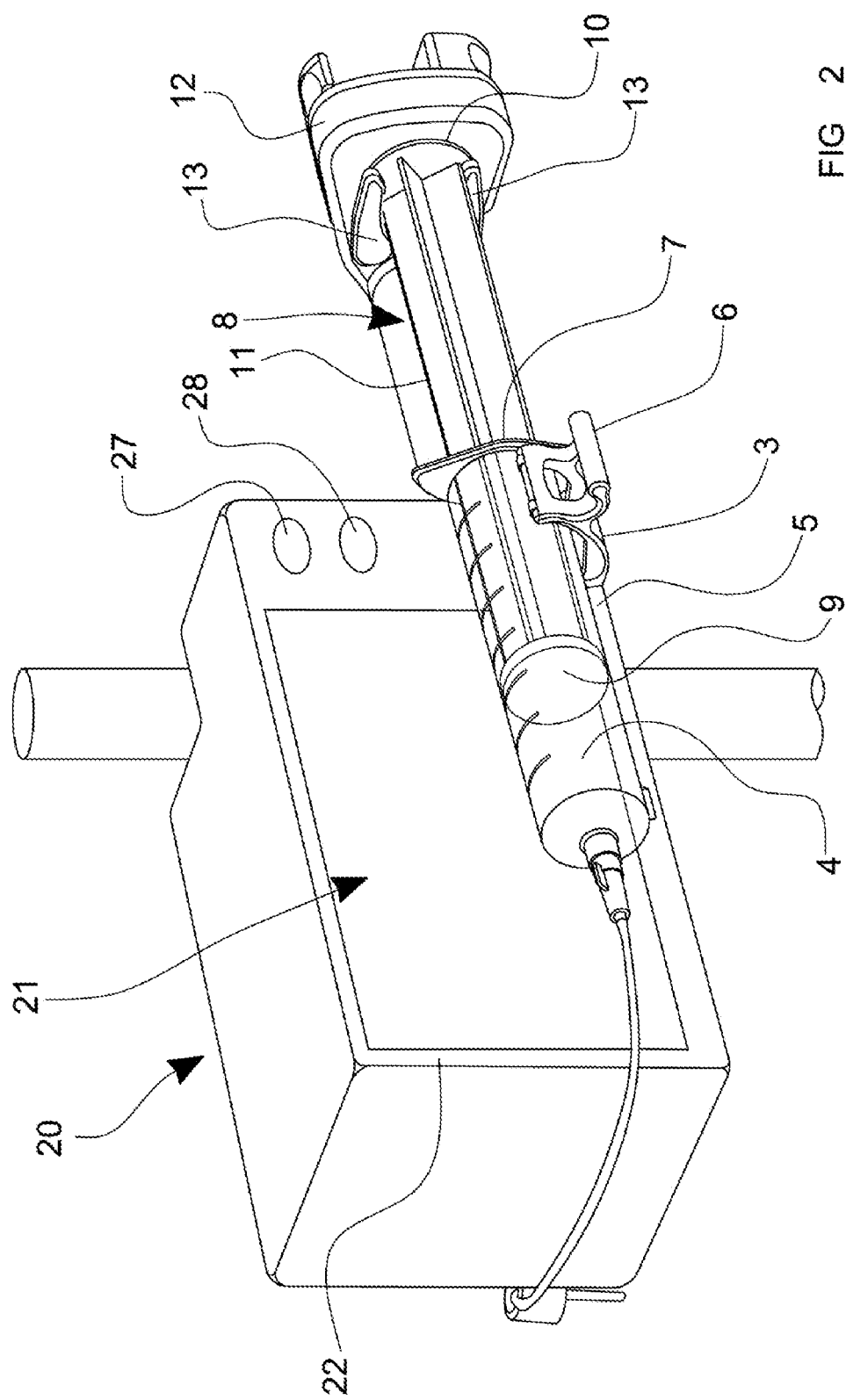
FIG. 2 is a perspective view of a syringe pump according to the present invention.
Figure 3:
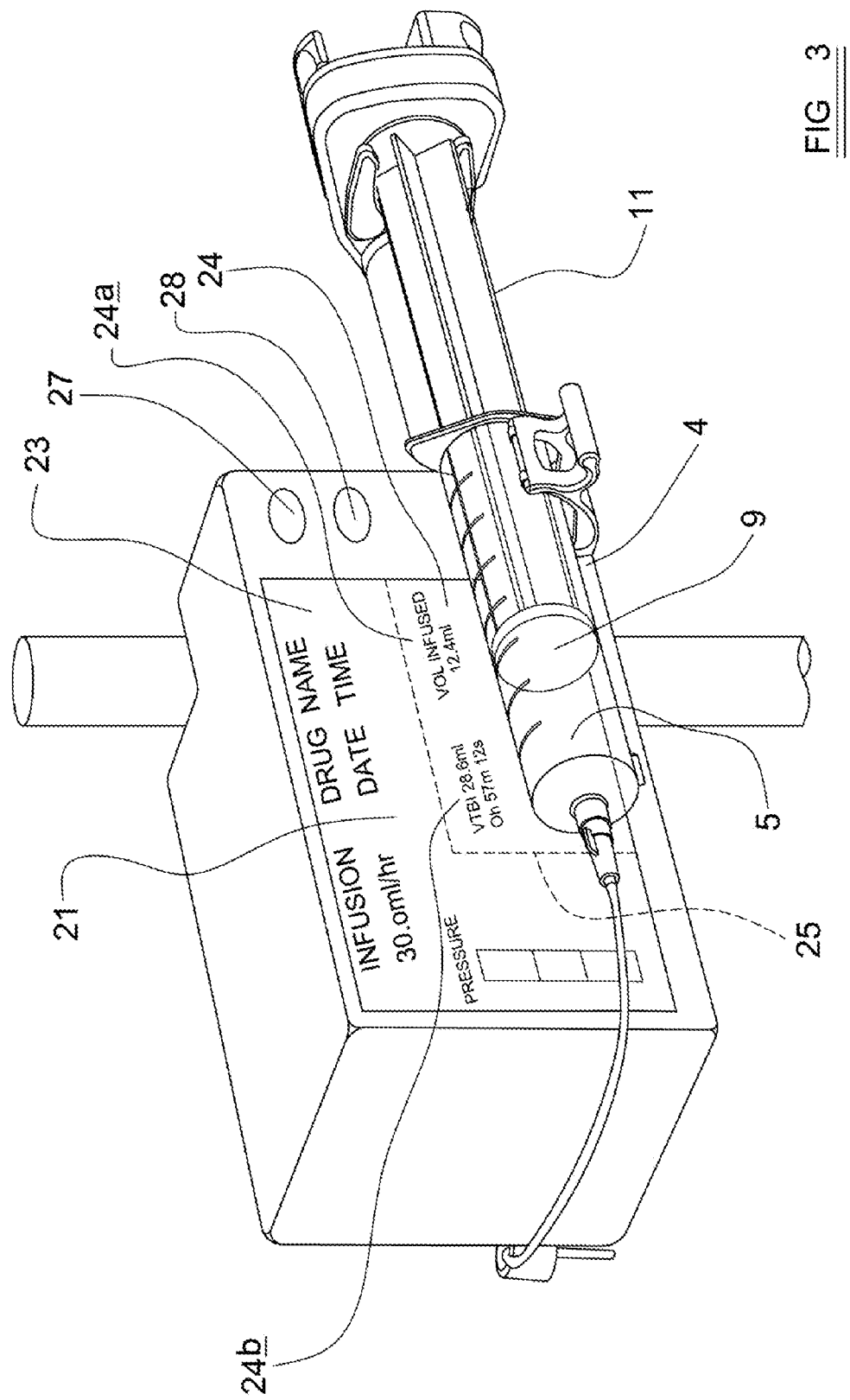
FIG. 3 is a perspective view corresponding to the syringe pump of FIG. 2.

The syringe pump 20 according to the present invention is shown in FIGS. 2 and 3. This syringe pump incorporates a display 21 having a commercially available LCD and, as can be seen from FIG. 2, in the syringe pump 20 of the invention, the syringe barrel 5 is positioned in front of part of the LCD.

As illustrated, the invention includes a standard 5.7 inch (145 mm) (diagonal dimension) TFT LCD. A TFT is a thin-film transistor, known in the art and well known in LCD technology. 5.7 inch TFT panels having a diagonal size of 5.7 inch are a standard size in the art and can be purchased from numerous manufacturers. Pixel resolution in a 5.7 inch TFT display can be, for example, 640×480 pixels. A typical "off the shelf" 5.7 inch TFT panel has an overall size of around 127 mm (width)×100 mm (height), a viewing area of around 118 mm (width)×89.5 mm (height) and an active area of approximately 115 mm (width)×86.5 mm (height). The diagonal length is therefore approximately 144-145 mm.

Resolution of a 5.7 inch TFT panel may be, for example, 640×480 pixels, and the panel may be capable of displaying 256K colours.

In the present invention the LCD display 21 covers a large proportion of the front facing housing 22 of the infusion pump 20. In particular, the LCD 21 extends over a large proportion of the height (short axis) of the front facing housing 22: preferably more than 80% thereof, more preferably at least 90 or 95% thereof, so that at least the top and bottom edges of the LCD panel 21 are as close as possible to the top and bottom edges of the front of the housing 22 of the pump 20. This allows the provision of a relatively large display 21 whilst minimising the front-facing surface area of the pump 20. Having a small unit size for the pump 20 is advantageous in the clinical setting, because this saves space around the patient. As will be explained later, having a small unit size is also advantageous when considering that several pumps may be mounted together in parallel.

The LCD display 21 displays infusion information on a zone 23 of the screen 21 not obscured by the syringe barrel 5. This could be, for example, an indication of the infusion rate, an indication that the system pressure is within safe limits, an indication of the drug name and an indication of the present time and date. These are illustrated in FIG. 3.

The LCD can also show an indication of the volume of liquid already infused, an indication of the volume still to be infused (VTBI) and an indication of the time already elapsed and infusion time remaining.

As known in the art, when programming a syringe pump, the user must input the type of syringe 4 being fitted to the pump. The pump stores in an internal memory a database of known syringe types containing information such as syringe diameter and stroke. The infusion pump firmware calculates the position of the syringe plunger and syringe piston based on movement of the syringe driver head and the type and size of the syringe. This allows the machine to display the calculation of volume infused, time elapsed, volume remaining and time remaining. As infusion continues and the driver head moves, these calculations can be updated and the displayed information changed.

As will be appreciated, by having a indication of volume already infused and time already elapsed displayed on a part 24a of the screen 21 proximal to the plunger stem 11, and an indication of the volume remaining and time remaining displayed on the screen 21 in the region 24b of the syringe barrel 5 beyond the end of the syringe piston 9, will provide a strong association to the user between the information displayed on the screen and the visual information from the syringe itself. Therefore, there is a strong correlation between the calculated data displayed on the screen and the visual state of the syringe. The correlation between data is much stronger than in prior art pumps, in which the screen is spatially more remote and dissociated from the syringe itself.

As the LCD is backlit, the back lighting also enhances the user's view of the syringe barrel 5, thereby providing a better visual indication of the actual state of infusion.

Furthermore, the TFT LCD can be "zoned" into, for example, areas of different colour or different brightness. For example, as shown, there is a separate coloured zone 25 in the region of the syringe barrel 5 which therefore backlights the syringe barrel 5 in a different colour to the rest 26 of the screen 21 and provides a better contrast. A separate zone is shown schematically within a dotted line 25 in FIGS. 3 and 4.

Preferably, the TFT LCD is also a touchscreen such as a capacititive touchscreen. Therefore, as shown, the syringe pump 20 only has one mechanically operated on/off switch 27 and a power light 28. Other inputs to the syringe pump, such as those described above in respect of the prior art, can be achieved by touching the touch screen. Therefore, when an operator sets up the syringe pump prior to an infusion, he or she can input for example, the drug name, infusion rate and syringe identity (size/manufacturer/volume) by touching pre-programmed regions of the touch screen. The syringe pump is provided with software to control the LCD touchscreen and to allow an operator to make these inputs.

More preferably, the user can manually set a point at which the syringe pump provides an alarm when the infusion is nearly finished. For example, if the operator wished to receive an alarm five minutes before the end of infusion, then the user could touch a region of the TFT LCD adjacent the syringe barrel 5 at the desired point, i.e. the user wishes to receive an alarm when the syringe piston 9 reaches that point. When the syringe piston 9 reaches this point, calculated by the movement of the driver head, then an alarm would sound or a visual alarm given on the screen.

Figure 4:
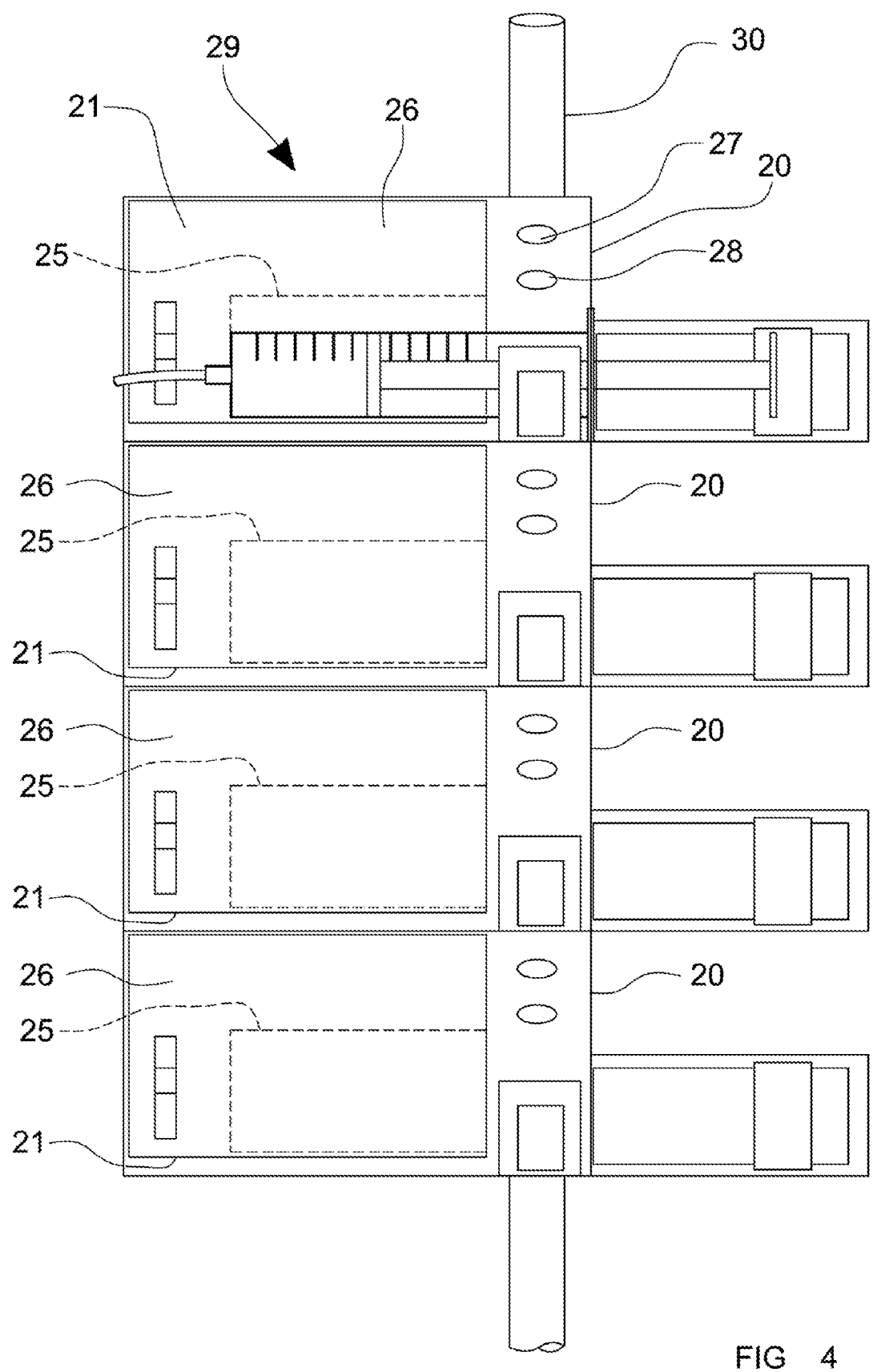
FIG. 4 is a front depiction of an array of syringe pumps according to the present invention.

In addition, as known in the prior art, syringe pumps may be provided in an array 29 as shown in FIG. 4. That is to say that a number of syringe pumps 20 may be mounted together for example on a mounting assembly such as a "T"-piece or pole 30. This means that a number of infusions can be carried out from separate syringe pumps 20, either simultaneously or sequentially, optionally under the control of a separate control module.

As known in the art, there exist "docking stations" which include several docking positions in which to park more than one syringe pump, together with the optional control unit, to which all of the pumps are connected. Typically, such docking stations bring several infusion pumps into close proximity with each other.

In prior art embodiments, the prior displays of each individual pump within an array were spatially apart from each other. On the contrary, when using the syringe pump 20 of the present invention, having a large LCD screen 21 which covers a large proportion of the front face 22 of the pump, and which extends nearly to the top and bottom edges of the front face, when several pumps 20 are aligned in an array 29, also the individual displays 21 aligned form a master display array which overall can provide a large area for the presentation of clinical data.

For example, whilst each display 21 provides information as outlined above relating to infusion from the syringe pump 20 containing that display, when combined together the master display can provide important messages relating to the infusion array 29. For example, if there was a mains power failure (power outage), then the master display array (consisting of the individual LCD elements) could display a warning prominently. Having a master array displaying such information is more noticeable to a user than having a single display or several discrete displays presenting this information.

Furthermore, if one individual pump 20 within the array needs particular attention, then the entire master display array could overall indicate that user intervention is required on a particular pump, whilst also displaying additionally on the particular pump that required attention, which action is needed (for example if a particular infusion pump were to become jammed or were some other problem to occur).

In addition, during a "relay" operation in which one syringe pump hands over infusion to a further pump, then the display screens of the two pumps could be combined to better communicate to the operator what is happening.

For example, where it is necessary to infuse large volumes over a long period of time, it would not be possible to provide a syringe large enough in one pump to achieve the desired infusion. Therefore, two pumps acting in relay in communication with each other would be required. When the first infusion from one syringe is completed, then the second syringe pump takes over. The display screens of the two pumps could be combined to display not only the infusion time remaining and volume to be infused from each individual pump but also the combined volume to be infused and time remaining from both pumps.

Accordingly, the present invention provides a syringe pump 20 having an improved display 21. The display not only provides back lighting of the syringe barrel 5 but also provides infusion data next to the syringe barrel to give a more intuitive set of information to the operator. When used in an array 29, the combined effect of the syringe pump displays allows a much larger area for displaying information relating a series of infusion pumps.

When used in this specification and claims, the terms "comprises" and "comprising" and variations thereof mean that the specified features, steps or integers are included. The terms are not to be interpreted to exclude the presence of other features, steps or components. The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A syringe pump comprising:
 a housing comprising an electronic display, a syringe retainer, and a plunger driver;
 the syringe retainer being held in a fixed position relative to the electronic display by the housing to fixedly retain a substantial portion of a barrel of a syringe in a fixed position located adjacent to and superimposed over the electronic display such that, when the electronic display is activated, at least the substantial portion of the barrel of the syringe is illuminated by a backlight provided by the electronic display behind the substantial portion of the barrel; and
 the electronic display comprising an array of pixels and operable to divide the electronic display into a first zone of the electronic display and a second zone of the electronic display spanning a length equivalent to at least the substantial portion of the barrel of the syringe when the syringe is retained by the syringe retainer and superimposed over the electronic display, wherein, when the electronic display is activated, the second zone is illuminated by the pixels with a different color than the first zone, and the barrel of the syringe, when the syringe is retained by the syringe retainer, is illuminated in the different color by the second zone of the electronic display behind the substantial portion of the barrel.

2. The syringe pump of claim 1 wherein the height of the electronic display ranges from 80% to 95% of the height of the housing.

3. The syringe pump of claim 1 wherein all of the pixels illuminating the first zone are located further from the syringe than any of the pixels illuminating the second zone, and wherein data displayed in the first zone includes at least one from the group consisting of syringe volume, syringe manufacturer, infusion rate, system pressure, drug name, current time, and current date.

4. The syringe pump of claim 1 wherein data displayed in the second zone includes at least one from the group consisting of volume infused, elapsed time, volume remaining, and time remaining.

5. The syringe pump of claim 1 wherein:
the syringe further comprises the syringe barrel slidably engaged with a syringe piston,
the syringe piston is connected to a syringe stem adjacent the plunger driver;
the second zone further comprises a first area and a second area;
the first area is behind the syringe barrel and beyond the syringe piston; and
the second area is behind the syringe barrel and proximate the syringe stem.

6. The syringe pump of claim 5 wherein data displayed in the first area includes at least one from the group consisting of volume remaining and time remaining.

7. The syringe pump of claim 5 wherein data displayed in the second area includes at least one from the group consisting of volume infused and elapsed time.

8. The syringe pump of claim 1 wherein the electronic display is a touchscreen.

9. The syringe pump of claim 1 further comprising a programmable alarm.

10. The syringe pump of claim 1 wherein the electronic display has a diagonal length of approximately 5.7 inches.

11. An array of syringe pumps comprising:
a plurality of syringe pumps positioned adjacent one another on a mounting assembly;
wherein each syringe pump of the plurality of syringe pumps comprises:
a housing comprising an electronic display, a syringe retainer, and a plunger driver;
the syringe retainer being held in a fixed position relative to the electronic display by the housing to fixedly retain a substantial portion of a barrel of a syringe in a fixed position located adjacent to and superimposed over the electronic display such that, when the electronic display is activated, at least the substantial portion of the barrel of the syringe is illuminated by a backlight provided by the electronic display behind the substantial portion of the barrel; and,
the electronic display comprises an array of pixels, fixedly arranged relative to each other, and operable to divide the electronic display into a first zone of the electronic display and a second zone of the electronic display spanning a length equivalent to at least the substantial portion of the barrel of the syringe when the syringe is retained by the syringe retainer and superimposed over the electronic display, wherein, when the electronic display is activated, the second zone is illuminated by the pixels with a different color than the first zone, and wherein when the electronic display is activated, the second zone is illuminated by the pixels with a different color than the first zone, and the barrel of the syringe, when the syringe is retained by the syringe retainer, is illuminated in the different color by the second zone of the electronic display behind the substantial portion of the barrel.

12. The array of syringe pumps of claim 11 wherein the mounting assembly is chosen from the group consisting of a T-piece or a pole.

13. The array of syringe pumps of claim 11 wherein data displayed in the first area includes at least one from the group consisting of volume remaining and time remaining.

14. The array of syringe pumps of claim 11 wherein data displayed in the second area includes at least one from the group consisting of volume infused and elapsed time.

15. The array of syringe pumps of claim 11 where the electronic display of at least one syringe pump of the plurality of syringe pumps has a diagonal length of approximately 5.7 inches.

16. A method of using a syringe pump to infuse medication to a patient, the method comprising:
providing a housing comprising a syringe retainer and a plunger driver;
providing the syringe retainer held in a fixed position by the housing to fixedly retain a substantial portion of a barrel of a syringe in a fixed position located adjacent to and superimposed over the electronic display such that, when the electronic display is activated, at least the substantial portion of the barrel of the syringe is illuminated by a backlight provided by the electronic display behind the substantial portion of the barrel;
providing a display in the housing where the display comprises an array of pixels operable to divide the electronic display into a first zone of the electronic display and a second zone of the electronic display spanning a length equivalent to at least the substantial portion of the barrel of the syringe when the syringe is retained by the syringe retainer and superimposed over the electronic display, where, when the electronic display is activated, the second zone is illuminated by the pixels with a different color than the first zone, and the barrel of the syringe is illuminated in the different color by the second zone of the electronic display behind the substantial portion of the barrel;
programming the syringe pump with the type of syringe, medication, and rate of infusion;
displaying data in the first zone, where the data displayed in the first zone is chosen from the group consisting of syringe volume, syringe manufacturer, infusion rate, system pressure, drug name, current time, and current date;
displaying data in the second zone, where the data displayed in the second zone is chosen from the group consisting of volume infused, elapsed time, volume remaining, and time remaining; and
providing a correlation between the data displayed in the second zone and the state of the medication within the syringe.

17. The method of claim 16 further comprising:
setting an alarm to signal near completion.

18. The method of claim 16 wherein the second zone comprises a first region and a second region, where the first region is behind the syringe barrel and beyond the syringe piston and wherein the second area is behind the syringe barrel and proximate the syringe stem.

19. The method of claim 18 further comprising: displaying data in the first region, wherein the data displayed in the first region includes at least one from the group consisting of volume remaining and time remaining.

20. The method of claim 18 further comprising: displaying data in the second region wherein the data displayed in the second region includes at least one from the group consisting of volume infused and elapsed time.

* * * * *